United States Patent [19]

Douglas et al.

[11] 4,393,077
[45] Jul. 12, 1983

[54] 1-METHYLENE-1-PHENYLGUANIDINE COMPOUNDS

[75] Inventors: George H. Douglas, Malvern; Henry F. Campbell, Lansdale, both of Pa.

[73] Assignee: William H. Rorer, Inc., Fort Washington, Pa.

[21] Appl. No.: 280,072

[22] Filed: Jul. 2, 1981

[51] Int. Cl.³ ............... A61K 31/155; C07C 129/08
[52] U.S. Cl. .................................. 424/326; 424/251; 424/273 R; 544/165; 544/224; 544/335; 544/336; 544/400; 544/216; 546/231; 546/332; 548/567; 549/494; 560/34; 562/439; 544/47; 544/238; 544/239
[58] Field of Search ............... 564/238, 237, 239; 424/326, 251, 273 R

[56] References Cited

U.S. PATENT DOCUMENTS 3,914,306 10/1975 Douglas et al. ............... 564/238
4,277,487 7/1981 Stahle et al. .................. 564/238

OTHER PUBLICATIONS

Goodman and Gilman's, *The Pharmacological Basis of Therapeutics*, 6 Ed. (1980), MacMillan Publ. (RS187 .G6), pp. 216–217.
*Stedman's Medical Dictionary*, (1980), pp. 567–569, The Williams & Wilkins Company, Publ.

Primary Examiner—Natalie Trousof
Assistant Examiner—Hendriksen L.
Attorney, Agent, or Firm—James A. Nicholson; Austin R. Miller; John Lezdey

[57] ABSTRACT

Compounds having the formula:

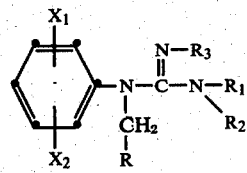

wherein $X_1$, $X_2$, R, $R_1$, $R_2$ and $R_3$ are as set forth hereinafter, their preparation and uses as ganglionic blocking agents are disclosed.

4 Claims, No Drawings

1-METHYLENE-1-PHENYLGUANIDINE COMPOUNDS

BACKGROUND OF THE INVENTION (a) Field of the Invention

This invention relates to 1-methylene-1-phenylguanidine compounds useful as ganglionic blocking agents and to their preparation.

(b) Description of the Prior Art

Belgium Pat. No. 857, 778, issued on Oct. 5, 1979, to Boehringer Ingelheim, shows N-cycloalkyl-methylphenylaminoimidazolines compounds having analgesic and cardioactivity.

U.S. Pat. No. 4,113,776 of Cohen et al discloses the preparation of 1-(2-aminoethyl)-3-(2,6-dihalophenyl)-guanidines.

SUMMARY OF THE INVENTION

This invention relates to 1-methylene-1-phenylguanidines or salts thereof, useful as ganglionic blocking agents and to compositions therefor.

Another feature of the present invention relates to compositions containing an effective amount of 1-methylene-1-phenyl-dimethylguanidine compound or salt thereof and a pharmaceutically acceptable carrier.

In a method aspect, the invention relates to a method for ganglionic blocking which comprises the administration of a medicament comprising a pharmaceutically acceptable carrier and as the active component thereof, an effective amount of a ganglionic blocking 1-methylene-1-phenyl guanidine compound.

DESCRIPTION AND PREFERRED EMBODIMENT

This invention relates to 1-methylene-1-phenyl guanidine compounds or the pharmaceutically acceptable salts thereof.

This method also describes a method for ganglionic blocking and also novel therapeutic compositions therefor.

The compounds of this invention can be represented by the generic structure which is described by the general formula:

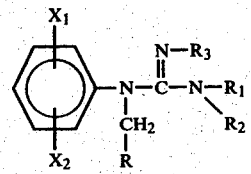

and the pharmaceutically acceptable salts thereof, wherein:

$X_1$ and $X_2$ are the same or different and each represent hydrogen, halo, trifluoromethyl, acyl, lower alkyl, hydroxy, lower alkoxy and amino;

$R_1$, $R_2$, and $R_3$ are the same or different and each represents hydrogen, lower alkyl, lower alkenyl, lower alkanoyl, and carbamoyl, and R represents cycloalkyl, cycloalkenyl, heterolower alkylidenyl and aryl;

Also, $R_3$ and either $R_1$ or $R_2$ can constitute a methylene bridge, —(CH$_2$)$_2$— or —(CH$_2$)$_3$—, resulting in the formation of a five- or six-membered ring.

In the descriptive portions of this invention the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid having up to 12 carbon atoms by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

"alkanoyl" refers to these acyl derivatives of a hydroxy-containing compound therein.

The preferred "aroyl" is benzoyl, loweralkylbenzoyl such as toluoyl or halobenzoyl such as—chlorobenzoyl, etc.

"alkoxy" refers to a lower alkoxy group containing from 1 to about 6 carbon atoms which may be straight, chained or branched.

"heteroloweralkylidenyl" refers to a loweralkylidenyl hydrocarbon group containing from about 2 to 5 carbon atoms and having one or more hetero atoms in the chain selected from O, N or S, such as piperidinyl, morpholinyl, etc.

Representative heteryl rings include such as thienyl, furyl, pyridyl, pyrazinyl, pyrimidinyl, pyridazinyl, triazinyl, isoxazolyl, isothiazolyl, pyrrolyl, imidazolyl, pyrazolyl, pyranyl, 2H-pyrrolyl, imidazolidinyl, imidazolinyl, pyrazolidinyl, pyrrolidinyl, pyrrolinyl, piperidyl, piperazinyl, morpholinyl.

It is well known in the pharmacological arts that non-toxic acid addition of salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc. and include such as:

| | |
|---|---|
| hydrochloric acid, | succinic acid, |
| hydrobromic acid, | glycolic acid, |
| sulfuric acid, | lactic acid, |
| nitric acid, | salicyclic acid, |
| phosphoric acid, | benzoic acid |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid, etc. |

The compounds of this invention may be prepared by the following general procedures. A N-carbonyl-aniline derivative is prepared by the reaction of an aniline compound with an acyl chloride compound in the presence of a hydrogen chloride scavenger, e.g. a tertiary amine, triethyl amine, or the like. The reaction is carried out under a variety of conditions, using procedures generally known in the art. Generally mild conditions are employed: 20°-60° C., contacting the reactants in a liquid medium (e.g. excess pyridine or an inert solvent such as benzene, toluene or chloroform).

The N-carbonyl-aniline derivative is reduced to the corresponding N-methylene-aniline compound, preferably, with a borohydride in a suitable solvent.

The N-methylene-aniline compound may be reacted with a cyanamide compound in a suitable solvent such as cresol, water or an alkanol in the presence of hydrogen chloride to yield 1-methylene-1-phenyl guanidine compounds of the present invention.

Additional compounds of this invention may be prepared by further treating the 1-methylene-1-phenyl guanidine compounds with either an acyl chloride compound or an isocyanate compound.

The following reaction scheme illustrate this synthesis:

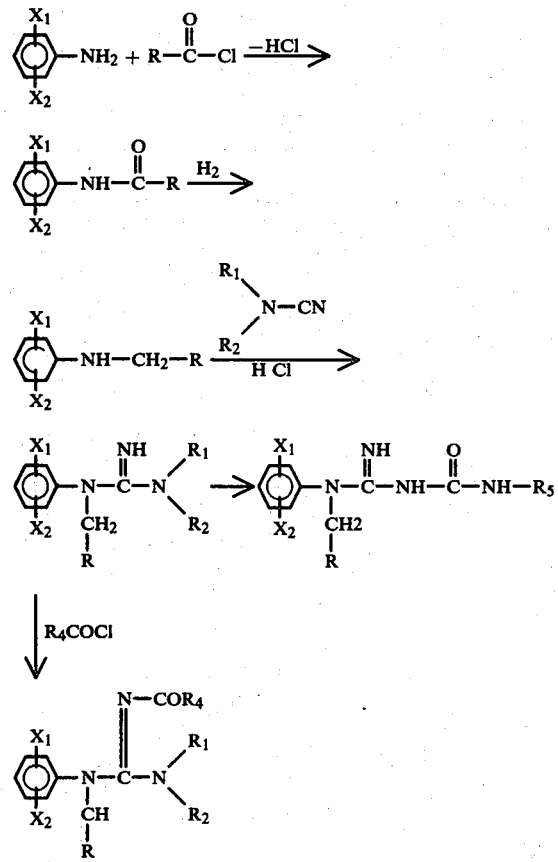

where $R_4$ is alkyl and $X_1$, $X_2$, R, $R_1$ and $R_2$ are as hereinbefore described.

The starting materials of this invention are either known compounds or their method of preparation is described.

We have found that the compounds of this invention have a useful degree of ganglionic blocking activity. It should further be noted that these compounds are also characterized by their low acute toxicity.

For all these purposes, the compounds of this invention can be normally administered parenterally. The term "parenteral" as used herein, includes subcutaneous injection, intravenous, intramuscular or intrasternal injection or infusion techniques.

The pharmaceutical compositions may be in the form of a sterile injectable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, these compounds may be formulated so that for every 100 parts by weight of the compositions, there are present between 5 and 95 parts by weight of the active ingredient. The dosage unit form will generally contain between about 1 mg and about 500 mg of the active ingredients of this invention. The preferred unit dose is between about 10 mg and about 100 mg.

The dosage regimen in carrying out the methods of this invention is that which insures maximum therapeutic response until improvement is obtained and thereafter the minimum effective level which gives relief. Thus, in general, the dosages are those that are therapeutically effective for ganglionic blocking activity. In general, the daily dose can be between about 0.5 mg/kg and 70 mg/kg (preferably in the range of 2-25 mg/kg/day), bearing in mind, of course, that in selecting the appropriate dosage in any specific case, consideration must be given to the patient's weight, general health, age, and other factors which may influence response to the drug.

The following are detailed Examples which show the preparation of the compounds of this invention. They are to be construed as illustrations of said compounds and not as limitations thereof.

EXAMPLE 1

N-cyclopropylcarbonyl-2,6-dichloroaniline 50.0 g. 2,6-dichloroaniline was dissolved in 300 ml. pyridine is a liter 3-necked flask equipped with magnetic stirrer, drying tube, thermometer, and addition funnel. 35.5 g. cyclopropane carboxylic acid chloride was added over a period of 20 minutes while maintaining a temperature of less than 35° C. with gentle water bath cooling. The mixture was then allowed to stir at room temperature for 1½ hours. The mixture was then poured into 500 ml. $CHCl_3$/500 ml $H_2O$. The layers were separated and the organic layer washed with water. The organic layer was then dried over sodium sulfate and evaporated in vacuo to yield a light brown solid.

The solid was dissolved in 350 ml warm methanol. This solution was then diluted with 350 ml. water and the warm mixture allowed to cool to room temperature. The precipitate which formed was filtered and the solid washed with 200 ml $NaOH/H_2O$(1:1). The precipitate was dried extensively under house vacuum at 70° C. Drying was continued overnight. 58.6 g (83%) of N-cyclopropylcarbonyl-2,6-dichloroaniline, a fluffy white solid was obtained. M.P. 166°–169° C.

EXAMPLE 2

When the procedure of Example 1 is followed but the 2,6-dichloroaniline is substituted by those below, then the corresponding product is obtained.

| Starting Material | Product |
|---|---|
| 2,6-dibromoaniline | N—cyclopropylcarbonyl-2,6-dibromoaniline |
| 2,6-dimethyoxyaniline | N—cyclopropylcarbonyl-2,6-dimethyoxyaniline |
| 2,6-difluoroaniline | N—cyclopropylcarbonyl-2,6-difluoroaniline |
| 2,4-dimethoxyaniline | N—cyclopropylcarbonyl-2,4-dimethoxyaniline |
| 3-chloro-4-methoxyaniline | N—cyclopropylcarbonyl-3-chloro-4-methoxyaniline |
| 2,chloro-4-hydroxyaniline | N—cyclopropylcarbonyl-2-chloro-4-hydroxyaniline |
| 2-chloro-4-carboxyaniline | N—cyclopropylcarbonyl-2-chloro-4-carboxyaniline |
| 2-chloro-4-carbethoxyaniline | N—cyclopropylcarbonyl-2-chloro-4-carbethoxyaniline |
| 2,6-dicarbethoxyaniline | N—cyclopropylcarbonyl-2,6-dicarbethoxyaniline |
| 2-chloro-4-dimethyl-aminoaniline | N—cyclopropylcarbonyl-2-chloro-4-dimethylaminoaniline |
| 2,6-di(trifluoromethyl)aniline | N—cyclopropylcarbonyl-2,6-di(trifluoromethyl)aniline |
| 2,6-di-i-propylaniline | N—cyclopropylcarbonyl-2,6-di-i-propylaniline |
| 2,4-dichloroaniline | N—cyclopropylcarbonyl-2,4-dichloroaniline |
| 2,4-dibromoaniline | N—cyclopropylcarbonyl-2,4-dibromoaniline |
| 2,4-difluoroaniline | N—cyclopropylcarbonyl-2,4-difluoroaniline |
| 2,3-difluoroaniline | N—cyclopropylcarbonyl-2,3-difluoroaniline |
| 2,5-difluoroaniline | N—cyclopropylcarbonyl-2,5-difluoroaniline |
| 4-allylaniline | N—cyclopropylcarbonyl-4-allylaniline |
| 4-aminoaniline | N—cyclopropylcarbonyl-4-aminoaniline |
| 2-chloro-4-aminoaniline | N—cyclopropylcarbonyl-2-chloro-4-aminoaniline |
| 2-chloro-6-fluoroaniline | N—cyclopropylcarbonyl-2-chloro-6-fluoroaniline |
| 2-chloro-4-fluoroaniline | N—cyclopropylcarbonyl-2-chloro-4-fluoroaniline |
| 2-chloro-5-fluoroaniline | N—cyclopropylcarbonyl-2-chloro-5-fluoroaniline |
| 2-chloro-4-aminoaniline | N—cyclopropylcarbonyl-2-chloro-4-aminoaniline |
| 2-chloro-4-methoxyaniline | N— cyclopropylcarbonyl-2-chloro-4-methoxyaniline |
| 2-chloro-4-hydroxyaniline | N—cyclopropylcarbonyl-2-chloro-4-hydroxyaniline |

EXAMPLE 3

When the procedure of Example 1 is followed but the cyclopropane carboxylic acid is substituted by those below, then the corresponding product is obtained.

| Starting Material | Product |
|---|---|
| Benzoic acid | N—phenyl-carbonyl-2,6-dichloroaniline |
| cyclobutane carboxylic acid | N—cyclobutylcarbonyl-2,6-dichloroaniline |
| cyclopentane carboxylic acid | N—cyclopentyl-carbonyl-2,6-dichloroaniline |
| cyclohexane carboxylic acid | N—cyclohexyl-carbonyl-2,6-dichloroaniline |
| cycloheptane carboxylic acid | N—cycloheptyl-carbonyl-2,6-dichloroaniline |
| pyrrolidine carboxylic acid | N—pyrrolidinyl-carbonyl-2,6-dichloroaniline |
| piperidine carboxylic acid | N—piperidinyl-carbonyl-2,6-dichloroaniline |
| furan carboxylic acid | N—furyl-carbonyl-2,6-dichloroaniline |
| pyridine carboxylic acid | N—pyridinyl-carbonyl-2,6-dichlroaniline |
| pyrazine carboxylic acid | N—pyrazinyl-carbonyl-2,6-dichloroaniline |
| pyrimidine carboxylic acid | N—pyrimidinyl-carbonyl-2,6-dichloroaniline |
| pyridazine carboxylic acid | N—pyridazinyl-carbonyl-2,6-dichloroaniline |
| triazine carboxylic acid | N—triazinyl-carbonyl-2,6-chloroaniline |
| morpholine carboxylic acid | N—morpholinyl-carbonyl-2,6-dichloroaniline |
| piperazine carboxylic acid | N—piperazinyl-carbonyl-2,6-dichloroaniline |

EXAMPLE 4

N-cyclopropylmethyl-2,6-dichloroaniline 58.4 grams of N-cyclopropylcarbonyl-2,6-dichloroaniline was dissolved in 550 ml of anhydrous tetrahydrofuran under a nitrogen atmosphere in a 2 liter 3-necked flask. The mixture was cooled in an ice bath to 4° C. To this mixture was added 389 ml of 0.9 M-diboronhexahydride in anhydrous tetrahydrofuran over a period of one hour and ten minutes while maintaining a temperature of less than 5° C. After addition was complete, the solution was allowed to warm to room temperature and stirred for one hour. The solution was then heated to reflux and reflux was maintained overnight. The solution was then cooled in an ice bath and 225 ml 6 N aqueous hydrogen chloride was added. This mixture was then evaporated in vacuo to remove the tetrahydrofuran. The resultant liquid and solid residue was diluted with 500 ml of water and cooled in an ice bath. 75 g of sodium hydroxide in 300 ml of water was then added. The mixture was then extracted with ether and the ether extract was washed twice with 500 ml of water, 250 ml of saturated saline solution and dried over sodium sulfate. The resultant mixture was then filtered and the filtrate was evaporated in vacuo. The resultant oil was dissolved in 100 ml of methanol and acidified with 250 ml of methanol/hydrogen chloride and then evaporated in vacuo at 35°–40° C. The resultant oil residue was dissolved in 250 ml of isopropanol and a crystalline precipitate formed. The reaction yielded 33.0 g of white solid N-cyclopropyl methyl-2,6-dichloroaniline having a melting point of 149°–158° C.

EXAMPLE 5

When the procedure of Example 4 is followed but the N-cyclopropyl carbonyl-2,6-dichloroaniline is substituted by the carbonyl compounds of Examples 2 and 3, then the corresponding N-methylene-aniline compound is obtained.

EXAMPLE 6

1-cyclopropylmethyl-1-(2,6-dichlorophenyl) guanidine 25.3 g of the N-cyclopropylmethyl-2,6-dichloroaniline hydrochloride was dissolved/suspended in 63 ml m-cresol. Anhydrous hydrogen chloride gas was bubbled in for 30 seconds. To this mixture was added 4.4 g cyanamide. This mixture was then heated on a steam bath, with occasional swirling for 2 hours. The mixture was then cooled and poured into 800 ml of ether, giving a dark gummy mass which solidified.

The solid was collected by filtration and washed with ether. The resulting dark chunks and crystalline material were dissolved in 100 ml warm ethanol. The mixture was filtered and the precipitate rinsed with 50 ml of ethanol. The filtrate was then diluted, with stirring with 750 ml anhydrous ether and stirred at room temperature for 30 minutes. This mixture was filtered and the solid washed with Et₂O/EtOH (1:5), and then with ether. The reaction yielded 16.9 g of white solid 1-cyclopropylmethyl-1-(2,6-dichlorophenyl)guanidine hydrochloride. M.P. 230°–231° C.

EXAMPLE 7

Following the procedure of Example 6, but substituting the N-methylene-aniline compounds of Example 5, there is obtained the corresponding guanidine compounds.

EXAMPLE 8

1-cyclopropylmethyl-1-(2,6-dichlorophenyl)-3,3-dimethylguanidine hydrochloride 21.4 g of N-cyclopropylmethyl-2,6-dichloroaniline hydrochloride was suspended in 53 ml of m-cresol and hydrogen chloride gas was bubbled into the mixture for 30 seconds. To this mixture was added 6.23 g of dimethylcyanamide and the resulting mixture was heated on a steam bath with occasional stirring for 2 hours. The mixture was then cooled and poured into about 1400 ml of anhydrous ether. The solid which formed was filtered and dissolved in 100 ml of warm isopropanol. The mixture was then cooled and filtered and the filtrate was poured into 400 ml of anhydrous ether. The solid which formed was filtered off and washed with isopropanol/ether (1:4). The ether portion was distilled off in vacuo and a white substrate formed. The precipitate was recrystallized in absolute methanol to yield 5.3 g of 1-cyclopropylmethyl-1-(2,6-dichlorophenyl)-3,3-dimethyl guanidine hydrochloride. M.P. 268°–269° C.

EXAMPLE 9

When the procedure of Example 8 is followed, but N-cyclopropylmethyl-2,6-dichloroaniline hydrochloride is replaced by any of the N-methylene-aniline compounds of Example 5, then the corresponding 1-methylene-1-phenyl-3,3-dimethyl guanidine compound is obtained.

EXAMPLE 10

1-cyclopropylmethyl-1-(2,6-dichlorophenyl)-3-methylcarbamoyl guanidine hydrochloride 11.5 g of 1-cyclopropylmethyl-1-(2,6-dichlorophenyl) guanidine hydrochloride was dissolved in 79 ml of water. The mixture was extracted twice with 100 ml of ether. The portion was washed with 50 ml of saturated saline solution at which point a crystalline solid began to precipitate. The mixture was diluted with 250 ml of dichloromethane, dried over sodium sulfate and evaporated in vacuo to yield 0.9 g of a clear near-colorless oil.

The oil was dissolved in 250 ml of anhydrous tetrahydrofuran, cooled in an ice bath, under a drying tube with stirring while adding 2.4 ml methyl isocyanate in 100 ml of tetrahydrofuran over a period of 2½ hours. The solution was then allowed to warm to room temperature over an hour. The solvent then evaporated in vacuo to yield a slightly cloudy oil. The oil which began to crystallize on standing was dissolved in 50 ml of methanol, then acidified with methanol/hydrogen chloride. The resultant solution was evaporated at about 35° C. The glass residue formed was dissolved in 50 ml of hot acetonitrile. The solution was filtered hot, rinsed with 20 ml CH₃CN and the solution was cooled with stirring in an ice bath, filtered and the solid washed with CH₃CN and then ether. The precipitate was dried under our vacuum at 46° C. to yield 10.0 g of white crystalline 1-cyclopropylmethyl-1-(2,6-dichlorophenyl)-3-methylcarbanoyl guanidine hydrochloride. M.P. 180°–182° C.

EXAMPLE 11

When the procedure of Example 10 is followed but the 1-cyclopropylmethyl-1-(2,6-dichlorophenyl) guanidine hydrochloride is substituted by the compounds of Example 7, then the following product may be obtained:

PRODUCT 1-cyclopropylmethyl-1-(2,6-dibromophenyl)-3-methylcarbamoyl guanidine hydrochloride 1-cyclopropylmethyl-1-(2,6-dimethoxyphenyl)-3-methylcarbamoyl guanidine hydrochloride.

1-cyclopropylmethyl-1-(2,6-difluoroaniline)-3-methylcarbamoyl guanidine hydrochloride.

1-cyclopropylmethyl-1-(2,4-dimethoxyphenyl)-3-methylcarbamoyl guanidine hydrochloride.

1-cyclopropylmethyl-1-(3,chloro-4-methoxyphenyl)-3-methylcarbamoyl guanidine hydrochloride.

1-cyclopropylmethyl-1-(2-chloro-4-methoxyphenyl)-3-methylcarbamoyl guanidine hydrochloride.

1-cyclopropylmethyl-1-(2-chloro-4-carboxyphenyl)-3-methylcarbamoyl guanidine hydrochloride.

1-cyclopropylmethyl-1-(2-chloro-carbethoxyphenyl)-3-methylcarbamoyl guanidine hydrochloride.

1-cyclopropylmethyl-1-(2,6-dicarbethoxyphenyl)-3-methylcarbamoyl guanidine hydrochloride.

1-cyclopropylmethyl-1-(2-chloro-4-dimethylaminophenyl)-3-methylcarbamoyl guanidine hydrochloride.

PRODUCT 1-cyclopropylmethyl-1-(2,6-di(trifluorophenyl)-3-methylcarbamoyl guanidine hydrochloride.

1-cyclopropylmethyl-1-(2,6-di-i-propylphenyl)-3-methylcarbamoyl guanidine hydrochloride.

1-cyclopropylmethyl-1-(2,4-dichlorophenyl)-3-methylcarbamoyl guanidine hydrochloride.

1-cyclopropylmethyl-1-(2,4-dibromophenyl)-3-methylcarbamoyl guanidine hydrochloride.

1-cyclopropylmethyl-1-(2,4-difluorophenyl)-3-methylcarbamoyl guanidine hydrochloride.

1-cyclopropylmethyl-1-(2,3-difluorophenyl)-3-methylcarbamoyl guanidine hydrochloride.

1-cyclopropylmethyl-1-(2,5-difluorophenyl)-3-methylcarbamoyl guanidine hydrochloride.

1-cyclopropylmethyl-1-(4-aminophenyl)-3-methylcarbamoyl guanidine hydrochloride.

1-cyclopropylmethyl-1-(4-allylphenyl)-3-methylcarbamoyl guanidine hydrochloride.

1-cyclopropylmethyl-1-(2-chloro-4-aminophenyl)-3-methylcarbamoyl guanidine hydrochloride.

1-cyclopropylmethyl-1-(2-chloro-6-fluorophenyl)-3-methylcarbamoyl guanidine hydrochloride.

1-cyclopropylmethyl-1-(2-chloro-4-fluorophenyl)-3-methylcarbamoyl guanidine hydrochloride.

1-cyclopropylmethyl-1-(2-chloro-5-fluorophenyl)-3-methylcarbamoyl guanidine hydrochloride.

1-cyclopropylmethyl-1-(2-chloro-4-aminophenyl)-3-methylcarbamoyl guanidine hydrochloride.

1-cyclopropylmethyl-1-(2-chloro-4-methoxyphenyl)-3-methylcarbamoyl guanidine hydrochloride.

1-cyclopropylmethyl-1-(2-chloro-4-hydroxyphenyl)-3-methylcarbamoyl guanidine hydrochloride.

1-phenylmethyl-1-(2,6-dichlorophenyl)-3-methylcarbamoyl guanidine hydrochloride.

1-cyclopentylmethyl-1-(2,6-dichlorophenyl)-3-methylcarbamoyl guanidine hydrochloride.

PRODUCT 1-cyclohexylmethyl-1-(2,6-dichlorophenyl)-3-methylcarbamoyl guanidine hydrochloride.

1-cycloheptylmethyl-1-(2,6-dichlorophenyl)-3-methylcarbamoyl guanidine hydrochloride.

1-pyrrolidinylmethyl-1-(2,6-dichlorophenyl)-3-methylcarbamoyl guanidine hydrochloride.

1-piperidinylmethyl-1-(2,6-dichlorophenyl)-3-methylcarbamoyl guanidine hydrochloride.

1-furylmethyl-1-(2,6-dichlorophenyl)-3-methylcarbamoyl guanidine hydrochloride.

1-pyridinylmethyl-1-(2,6-dichlorophenyl)-3-methylcarbamoyl guanidine hydrochloride.

1-pyrazinylmethyl-1-(2,6-dichlorophenyl)-3-methylcarbamoyl guanidine hydrochloride.

1-pyrimidinylmethyl-1-(2,6-dichlorophenyl)-3-methylcarbamoyl guanidine hydrochloride.

1-pyridazinylmethyl-1-(2,5-dichlorophenyl)-3-methylcarbamoyl guanidine hydrochloride.

1-triazinylmethyl-1-(2,6-dichlorophenyl)-3-methylcarbamoyl guanidine hydrochloride.

1-morpholinylmethyl-1-(2,6-dichlorophenyl)-3-methylcarbamoyl guanidine hydrochloride.

1-piperazinylmethyl-1-(2,6-dichlorophenyl)-3-methylcarbamoyl guanidine hydrochloride.

EXAMPLE 12

1,000 hard gelatin capsules, each containing 200 milligrams of 1-cyclopropylmethyl-1-(2,6-dichlorophenyl)-3-methylcarbamoyl guanidine are prepared from the following formulation:

| | Grams |
|---|---|
| 1-cyclopropylmethyl-1-(2,6-dichlorophenyl)-3-methylcarbamoyl guanidine | 200 |
| Starch | 250 |
| Lactose | 750 |
| Kaolin | 250 |
| Calcium stearate | 10. |

A uniform mixture of the ingredients is prepared by blending and employed to fill two-piece hard gelatin capsules. The capsules are suitable to be orally administered in accordance with this invention.

We claim:

1. A method for ganglionic blocking which comprises administering an effective amount of a compound of the formula

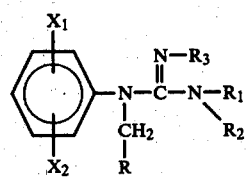

and the pharmaceutically acceptable salts thereof, wherein
$X_1$ and $X_2$ each represent a member selected from the group consisting of hydrogen, halo, trifluoromethyl, acyl, alkyl, hydroxy, alkoxy and amino,
$R_1$, $R_2$, and $R_3$ each represent a member selected from the group consisting of hydrogen, lower alkyl and lower alkenyl and
R represents a member selected from the group consisting of cycloalkyl, cycloalkenyl and aryl,
also, $R_3$ and either $R_1$ or $R_2$ can constitute a methylene bridge, —$(CH_2)_2$— or —$(CH_2)_3$—, resulting in the formation of a five- or six-membered ring.

2. The method according to claim 1, wherein the compound is 1-cyclopropylmethyl-1-(2,6-dichlorophenyl) guanidine.

3. The method according to claim 1, wherein the compound is 1-cyclobutylmethyl-1-(2,6-dichlorophenyl) guanidine.

4. The method according to claim 1, wherein the compound is 1-cyclohexylmethyl-1-(2,6-dichlorophenyl) guanidine.

* * * * *